United States Patent
Chung et al.

(10) Patent No.: US 7,371,416 B2
(45) Date of Patent: May 13, 2008

(54) METHOD FOR PREPARING PROCESSED GINSENG TO OBTAIN INCREASED AMOUNT OF GINSENOSIDE RG5

(75) Inventors: You-Sup Chung, #101-802 Neulpuren Byoksan Apt. Mangpo-dong Yeongtong, Suwon (KR) 443-707; Jin-Wha Choi, Suwon (KR)

(73) Assignee: You-Sup Chung, Suwon-si (KR)

( * ) Notice: Subject to any disclaimer, the term of this patent is extended or adjusted under 35 U.S.C. 154(b) by 3 days.

(21) Appl. No.: 11/295,111

(22) Filed: Dec. 6, 2005

(65) Prior Publication Data

US 2006/0228430 A1 Oct. 12, 2006

(30) Foreign Application Priority Data

Apr. 12, 2005 (KR) .................. 10-2005-0030519

(51) Int. Cl.
*A61K 36/258* (2006.01)

(52) U.S. Cl. ...................................... 424/728; 424/725

(58) Field of Classification Search .................... None
See application file for complete search history.

(56) References Cited

U.S. PATENT DOCUMENTS 5,776,460 A * 7/1998 Kim et al. .................. 424/728
2004/0009243 A1* 1/2004 Yun et al. ................... 424/728

FOREIGN PATENT DOCUMENTS

KR  2004020693 A * 3/2004

OTHER PUBLICATIONS

Kim et al. (J. Nat. Products (2000), vol. 63, pp. 1702-1704).*

* cited by examiner

*Primary Examiner*—Susan Coe Hoffman
(74) *Attorney, Agent, or Firm*—Kirk Hahn

(57) ABSTRACT

The present invention relates to a processing method for preparing pharmacologically potent ginseng product and the extract therefrom which could provide abundant amount ginsenoside Rg5 showing various pharmacological activities with applying selected range of pressure and temperature into the method and therefore the composition comprising the processed ginseng and the extract thereof can be useful as a medicament or health care food in the prevention or treatment of various diseases, especially, cancer disease.

17 Claims, 8 Drawing Sheets

Fig 8: Effect of extract solution (A) on the tumor incidence in mice treated with B16 cell line.

US 7,371,416 B2

METHOD FOR PREPARING PROCESSED GINSENG TO OBTAIN INCREASED AMOUNT OF GINSENOSIDE RG5

This application claims priority upon Korean. Patent application Ser. No. KR 10-2005-00305 19 filed on Apr. 12, 2005, the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

1. Technical Field

The present invention relates to a method for preparing novel processed ginseng to obtain increased amount of ginsenoside Rg5. More particularly, the present invention relates to a method for preparing processed ginseng product and the extract thereof which contains increased amount of ginsenoside Rg5 by treating ginseng under specific pressure and temperature range.

2. Background Art

It has been found that ginseng enforces non-specific resistance to psychological stress and shows maintaining effect on human homeostasis together with other potent pharmacological activities, i.e., alleviation of hypertension, reinforcing activity of insulin, blood glucose lowering activity, stimulating effect on liver RNA synthesis, protein, glucose and lipid metabolism or anticancer activity.

There are many genus of *Panax* genus plants belonged to Araliaceae, for example, *Panax ginseng* distributed or cultivated in far-eastern Asia region, *Panax quinquefolia* in America and Canada, *Panax notoginseng* in China, *Panax trifolia* in eastern region of north America, *Panax japonica* in Japan, China and Nepal, *Panax pseudoginseng* in Nepal, *Panax vietnamensis* in Vietnam, *Panax elegatior, Panax wangianus* and *Panax bipinratifidus* etc.

Three types of ginseng products have been commercially available i.e., four year's old, five year's and six year's old ginseng and six year's old ginseng product cultivated on autumn has been reported to most potent among them. Particularly, the husk of un-husked ginseng contains lots of saponin, which shows potent activity.

Ginsenosidal saponins isolated from ginseng having dammarane skeleton linked to several saccharides are different from those isolated from the other plants. In particular, there have been reported that ginseng contains about 30 kinds of saponin ingredients, especially ginsenoside Rb1, Rb2, Rc, Rd, Rg, Re etc as main components. Those saponin compounds shows various pharmacological activities and potency according to their chemical structure and ginsenoside Rg5 among them has been highlighted as a medicine due to its potent immuno-potentiating activity as well as vaso dilating activity, anti-cancer activity, neuronal cell protecting activity etc recently.

At present, there have been tried to process conventional ginseng to obtain more potent efficacy or utility by way of changing the structure of ginseng saponin in the process.

Korean Patent Registration No. 10-0192678, discloses a process for preparing a processed ginseng prepared by subjecting hot temperature treatment containing high contents of ginsenoside $Rg_5$ so as to obtaining processed ginseng having improved potency differing from original form of ginseng. However, the processing method could not provide the information on the correlation between the content change of ginsenoside Rg5 and the change of temperature and internal pressure and the method requires toxic organic solvent such as butanol.

The inventors of the present invention have intensively carried out the scientific investigation concerning new processing method to obtain safe and uniform ginseng product. As a result of the investigation, the inventors have found novel processing method for preparing pharmacologically potent ginseng product which have more increased content of ginsenoside Rg5 verified by comparing with conventional ginseng and the processed ginseng product disclosed in prior art and they have finally completed the present invention.

SUMMARY OF THE INVENTION

Accordingly, it is an object of the present invention to provide a processing method for preparing pharmacologically potent ginseng products which has increased content of ginsenoside Rg5.

DISCLOSURE OF THE INVENTION

In accordance with the present invention, the present invention provides a processing method for preparing pharmacologically potent ginseng product and the extract therefrom which obtain maximized content of ginsenoside Rg5 characterized in treating ginseng with selected ranges of pressure and temperature.

Specifically, the present invention provides a processing method for preparing pharmacologically potent ginseng product consisting of the steps comprising; adding about 1 to 2 times weight of water based on the weight of ginseng to five to seven years old ginseng material, preferably six year old ginseng material; and treating step under the internal pressure ranging from 1.10 to 3.50 $kgf/cm^2$, preferably, 1.40 to 1.50 $kgf/cm^2$ in case of un-husked ginseng or 2.80 to 3.00 $kgf/cm^2$ in case of husked ginseng in the temperature ranging from about 100 to 150° C., preferably 126 to 130° C. for a period ranging from 1 to 5 hrs, preferably, about 2 hrs to obtain purposed processed ginseng having large amount of ginsenoside Rg5.

Through the above-described processing method in case of un-husked ginseng, the final ginseng product of the present invention contains much more amount of ginsenoside Rg5, about two to five times, specifically about 4.4 times than the processed ginseng prepared from the method disclosed in Korean Patent Registration No. 10-0192678, Through the above-described processing method in case of husked ginseng, the final ginseng product of the present invention contains much more amount of ginsenoside Rg5, about two to five times, specifically about 3.3 times than the processed ginseng prepared from the method disclosed in Korean Patent Registration No. 10-0192678.

The present invention also provides a method for extracting the extract of processed ginseng consisting of the steps comprising: extracting processed ginseng material prepared from above described step with the mixture of organic solvent, preferably, the mixture of methanol and methylene chloride, more preferably, mixture of methanol and methylene chloride with the mixed volume ratio ranging from 0.60:1.40 to 1.20:0.80, more preferably, about 1:1 (v/v) mixture of methanol and methylene chloride with reflux extraction method in the period ranging from 1 hr to two days, preferably more than 1 hour; filtrating to obtain filtrate, concentrating the filtrate to remove remaining solvent and drying to obtain potent ginseng extract having large amount of ginsenoside Rg5.

The "ginseng material" disclosed herein aged six year old is preferably used in the present invention since six year old ginseng showed higher amount of ginsenoside Rg5 than four years old ginseng, which was confirmed by following experiments prosecuted by the present inventors.

The "ginseng material" disclosed herein comprise the leaf thereof which has been reported to be useless as well as root part of ginseng in the present invention since it is confirmed that the processed leaf of ginseng of the present invention showed equivalent amount of ginsenoside Rg5 to the root part of ginseng, which was confirmed by following experiments prosecuted by the present inventors.

The ginseng thus processed or the extract thereof may be dried by a known manner to obtain a dried processed ginseng, for example, dried at a lower temperature, i.e., below 70° C. for the period ranging from about 60 to 72 hrs or freeze-drying method and it may be further processed to be pulverized or powdered into the smaller size, preferably, the size ranging from about 50 to 200 micrometer by the method well-known in the art, if necessary, to prepare commercially available final product such as capsule, tablet etc using by pharmaceutically acceptable carrier or adjuvant.

The inventive processed ginseng of the present invention contains abundant ginsenoside Rg5 showing potent pharmacological activity such as vaso dilating activity, immunopotentiating activity, anti-cancer activity, neuronal cell-protecting activity etc, anti-cancer activity in particular.

Therefore, the present invention also provides a pharmaceutical composition comprising the ginseng extract prepared from the above-described processing method and a pharmaceutically acceptable carrier or adjuvants for the treatment or prevention of cancer disease and the method of the present invention can provide with maximized content of ginsenoside Rg5 by adopting selected ranges of pressure and temperature.

The term "cancer" disclosed herein comprises various cancers such as stomach cancer, liver cancer, lung cancer, cervical cancer or breast cancer.

The ginseng extract of the present invention has potent anticancer activity and therefore, the pharmaceutical composition of the present invention thus may be employed to treat or prevent various cancer diseases.

The present invention also provides a use of ginseng extract prepared from above-described processing method for manufacture of medicines employed for treating or preventing various cancer such as stomach cancer, liver cancer, lung cancer in men, and cervical cancer, breast cancer.

In accordance with another aspect of the present invention, there is also provided an method of treating or preventing various cancer such as stomach cancer, liver cancer, lung cancer in men, and cervical cancer, breast cancer, wherein the method comprises administering a therapeutically effective amount of the ginseng extract prepared from above-described processing method.

The inventive composition may additionally comprise conventional carrier, adjuvants or diluents in accordance with a using method. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

Pharmaceutical formulations containing present composition may be prepared in any form, such as oral dosage form (powder, latinor-pulves, granule, tablet, capsule, soft capsule, aqueous medicine, syrup, elixirs pill, solution, powder, sachet, granule), or topical preparation (cream, ointment, lotion, gel, balm, patch, paste, spray solution, aerosol and the like), or injectable preparation (solution, suspension, emulsion, injection).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or composition varies depending on the condition and the weight of the subject, severity, drug form, route and period of administration, and may be chosen by those skilled in the art. However, in order to obtain desirable effects, it is generally recommended to administer at the amount ranging 0.2 mg-200 mg/kg, preferably, 2 mg to 100 mg/kg by weight/day of the inventive extract or compounds of the present invention. The dose may be administered in single or divided into several times per day. In terms of composition, the complex herbal composition should be present between 0.01 to 80% by weight, preferably 0.5 to 50% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

Accordingly, it is another object of the present invention to provide a health care food comprising above described extract prepared by the above processing method and a sitologically acceptable additive to prevent various diseases.

Above described composition therein can be used for the prevention or alleviation of various cancer diseases. For the purpose of preventing or alleviating various cancer diseases, wherein, the amount of above described extract may generally range from about 0.1 to 15 w/w %, preferably 1 to 10 w/w % of total weight of food for the health food composition and 1 to 30 g, preferably 3 to 10 g on the ratio of 100 ml of the health beverage composition. The composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection in any form, such as oral dosage form (powder, latinor-pulves, granule, tablet, capsule, soft capsule, syrup, elixirs pill, solution, powder, sachet or granule).

Providing that the health beverage composition of present invention contains above described extract as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition.

Examples of addable food comprising aforementioned extract therein are various food, beverage, gum, vitamin complex, health care food and the like.

It will be apparent to those skilled in the art that various modifications and variations can be made in the compositions, use and preparations of the present invention without departing from the spirit or scope of the invention.

BRIEF DESCRIPTION OF THE DRAWINGS

The above and other objects, features and other advantages of the present invention will more clearly understood from the following detailed description taken in conjunction with the accompanying drawings, in which.

BEST MODE FOR CARRYING OUT THE INVENTION

Figure 1:
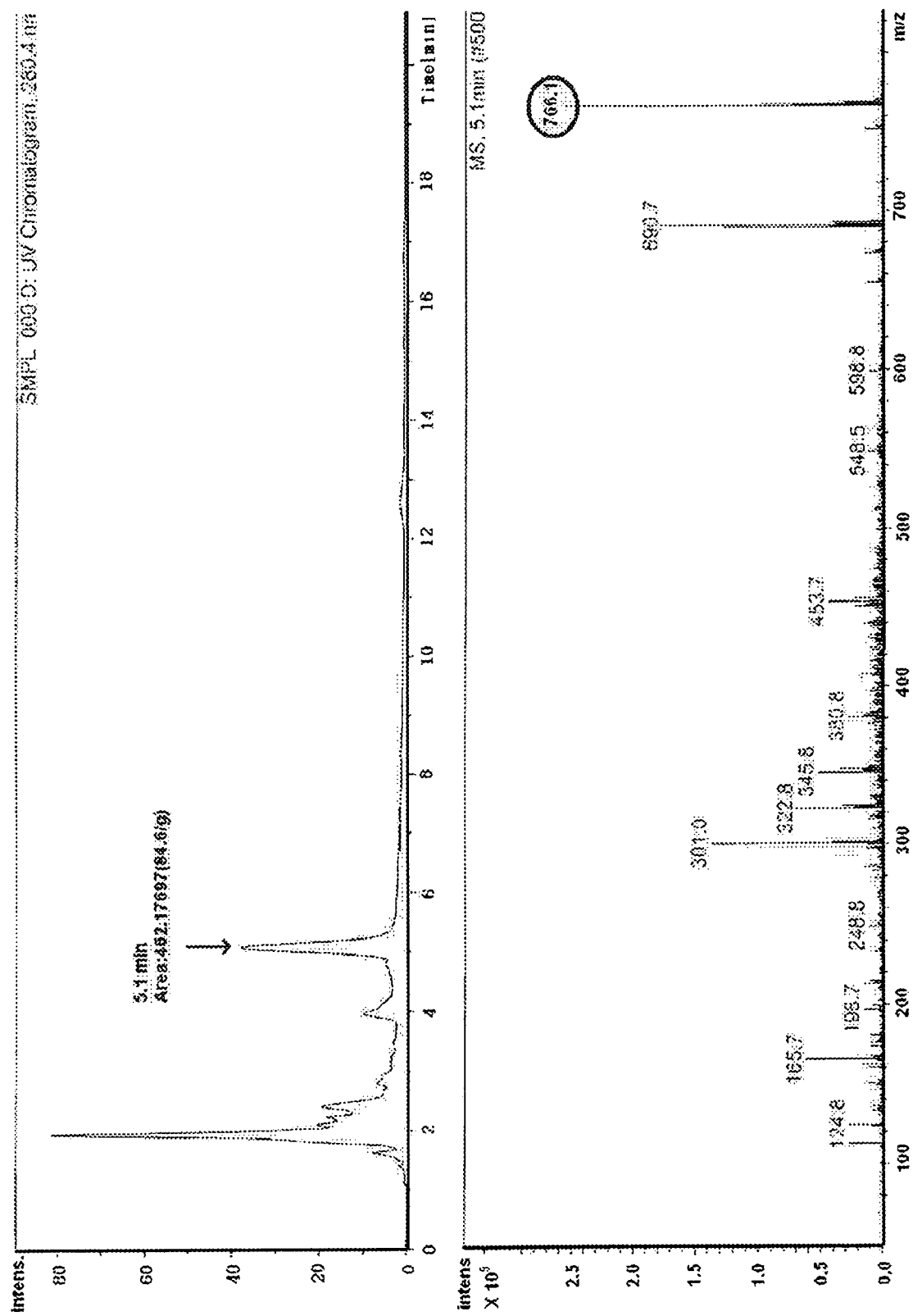
FIG. 1 shows the result of LC and Mass spectrum of ginseng extract (G1)
Figure 2:
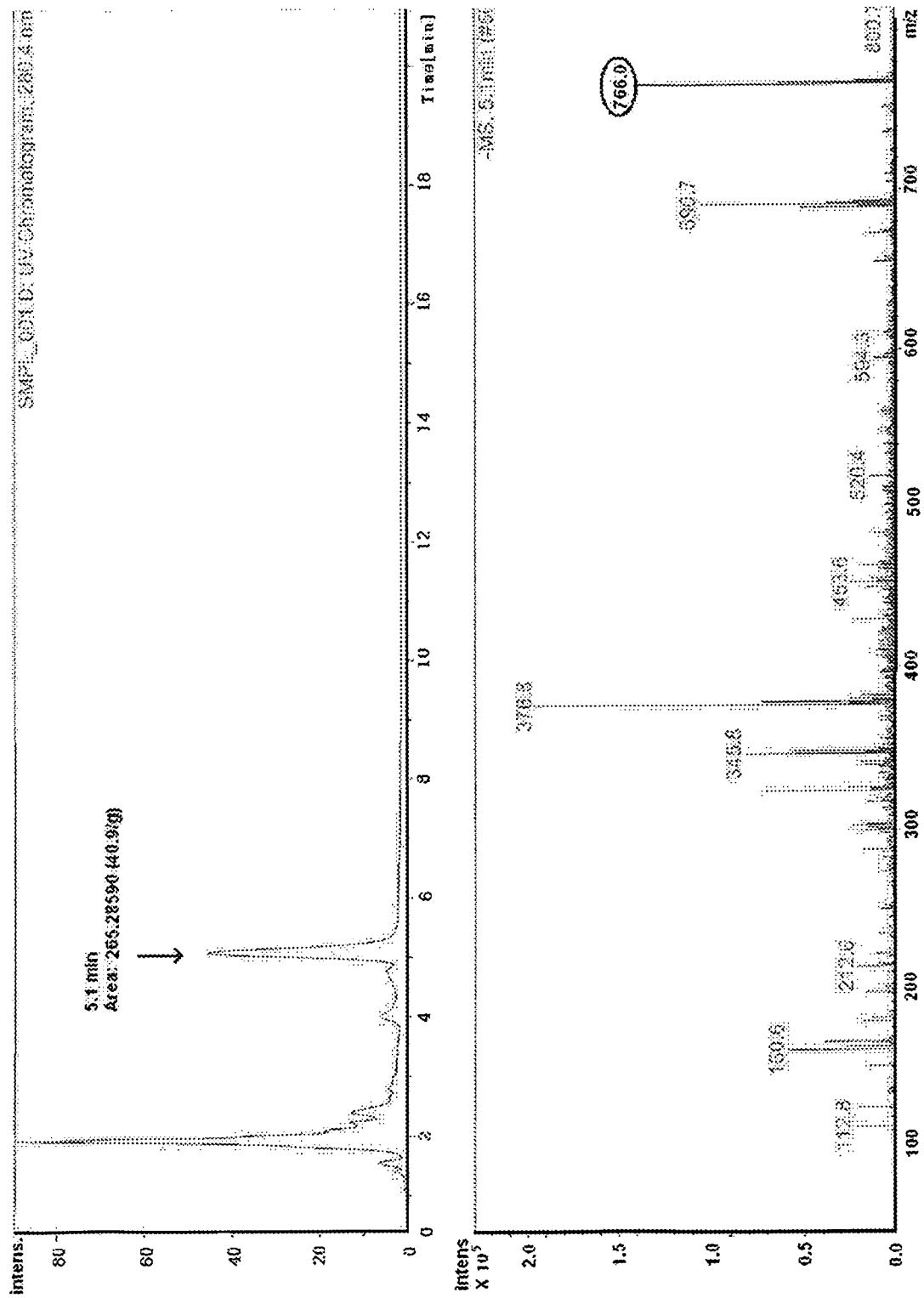
FIG. 2 shows the result of LC and Mass spectrum of ginseng extract (G2)
Figure 3:
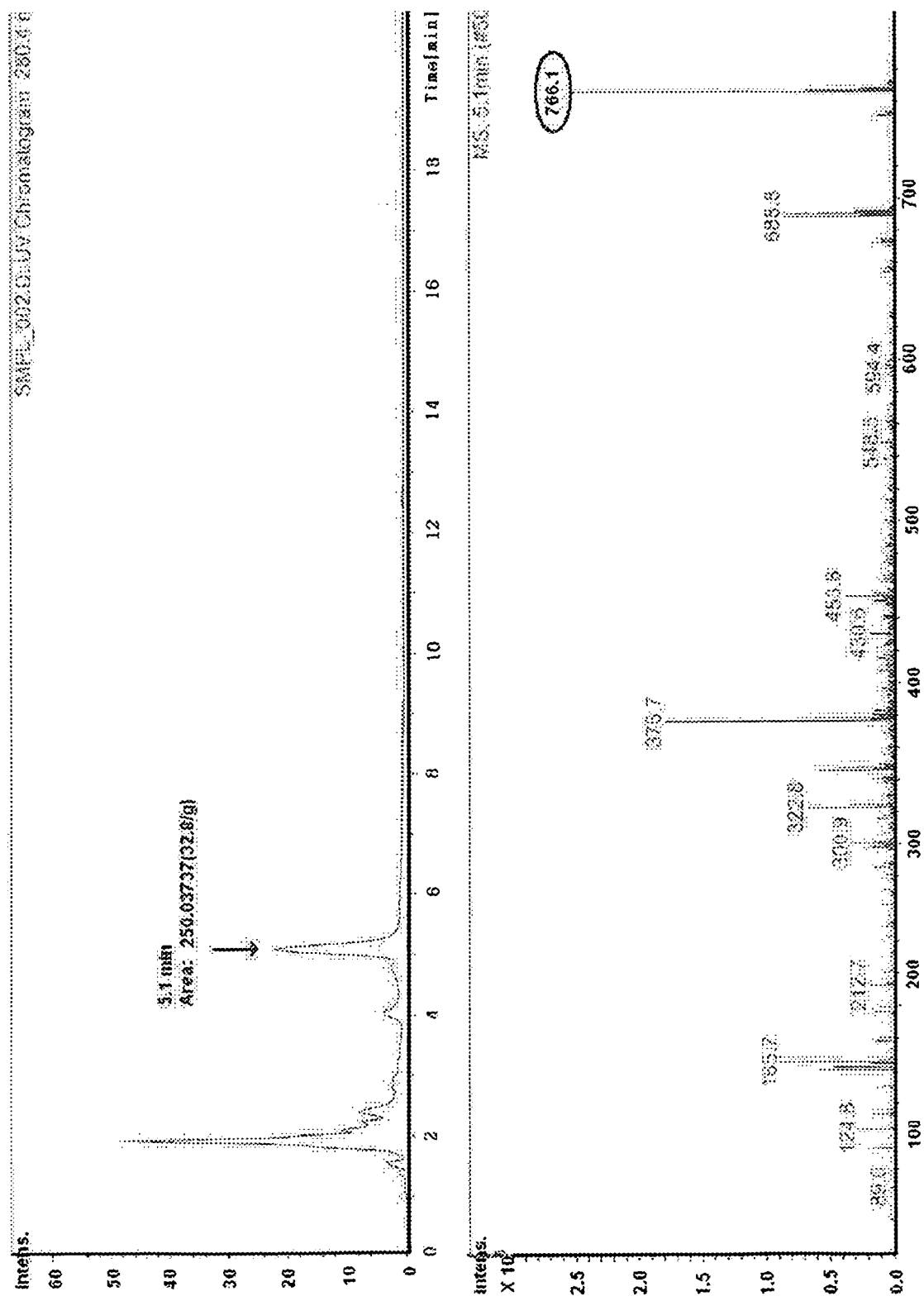
FIG. 3 shows the result of LC and Mass spectrum of ginseng extract (G3)
Figure 4:
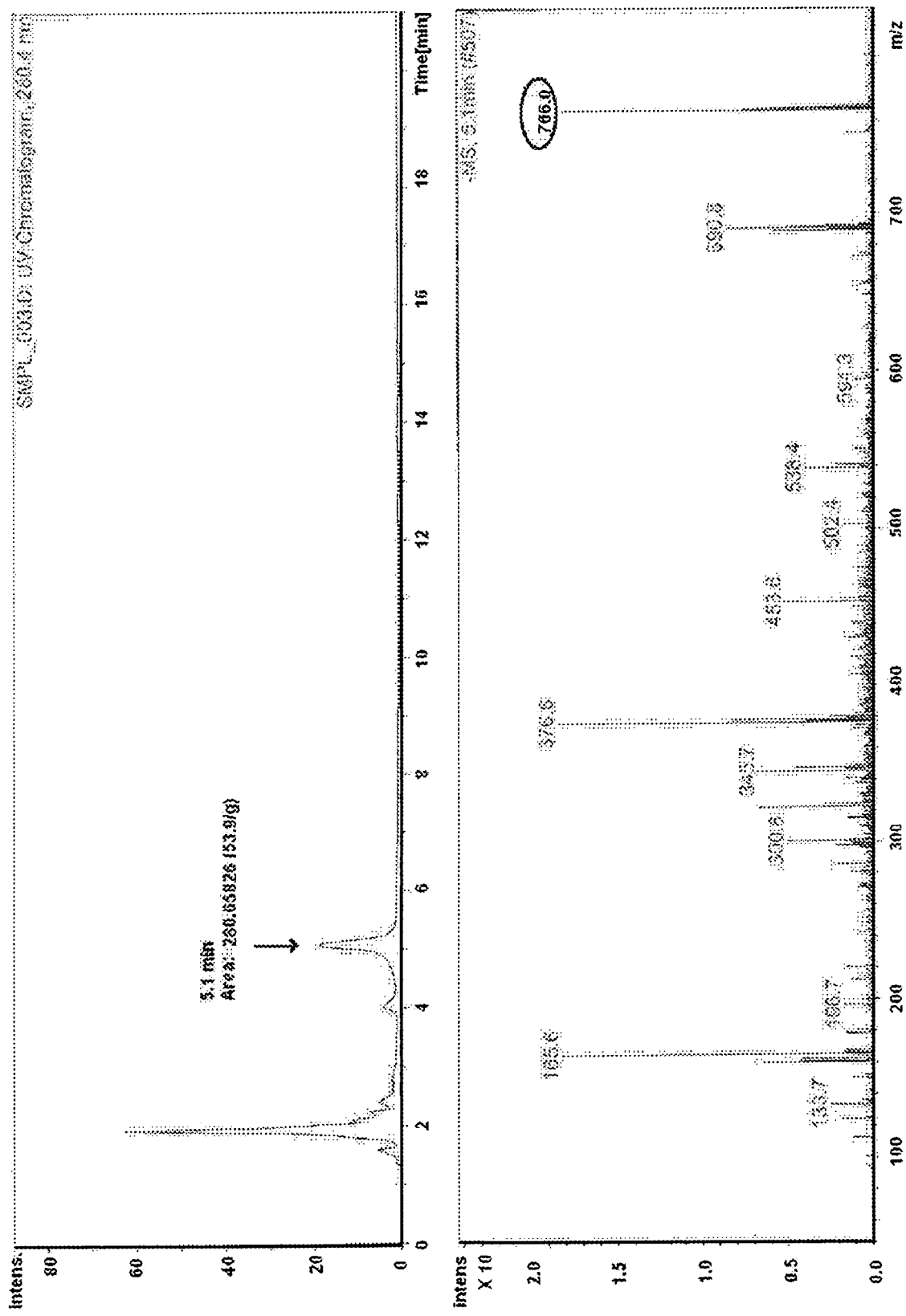
FIG. 4 shows the result of LC and Mass spectrum of ginseng extract (G4)
Figure 5:
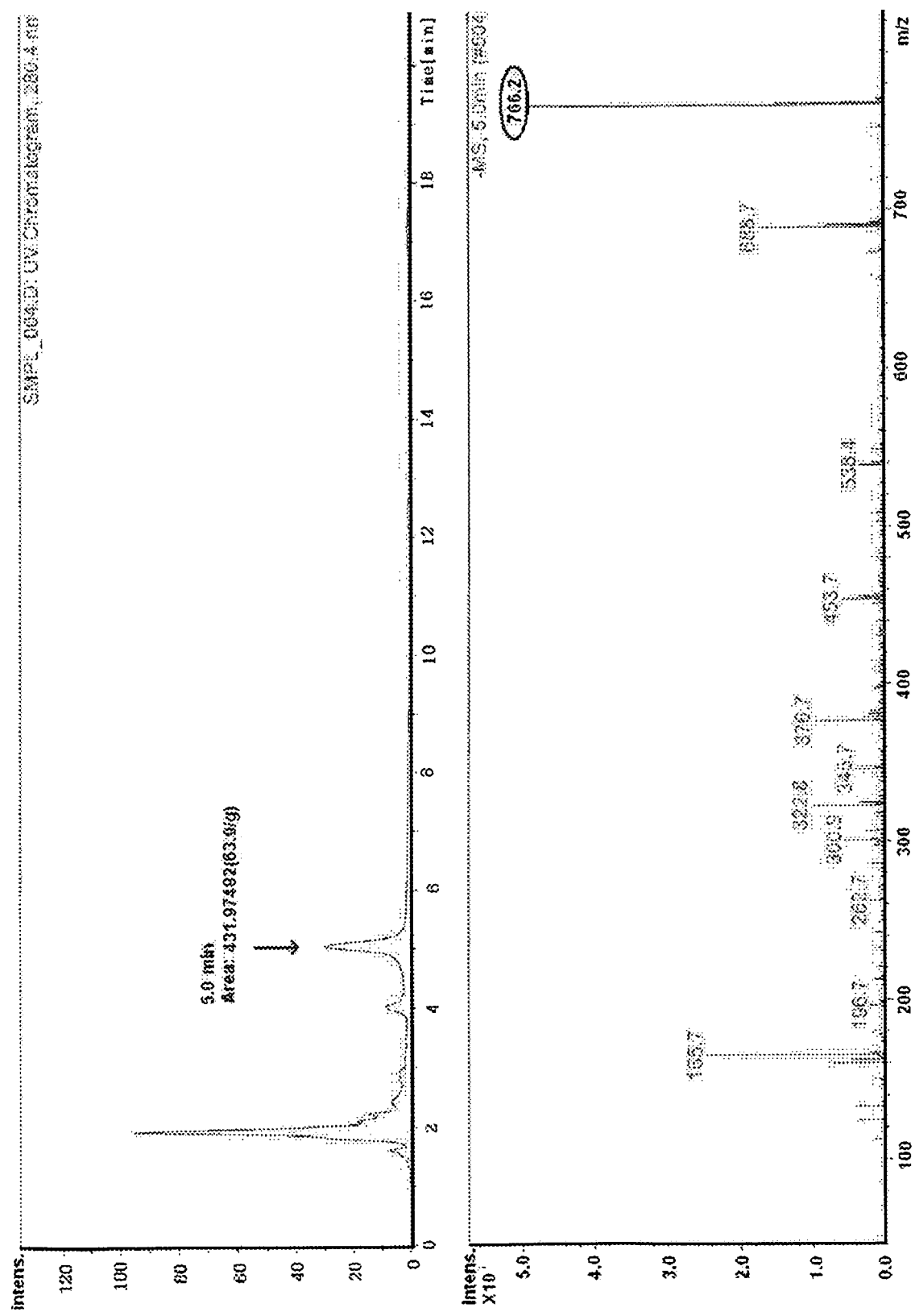
FIG. 5 shows the result of LC and Mass spectrum of ginseng extract (G5)
Figure 6:
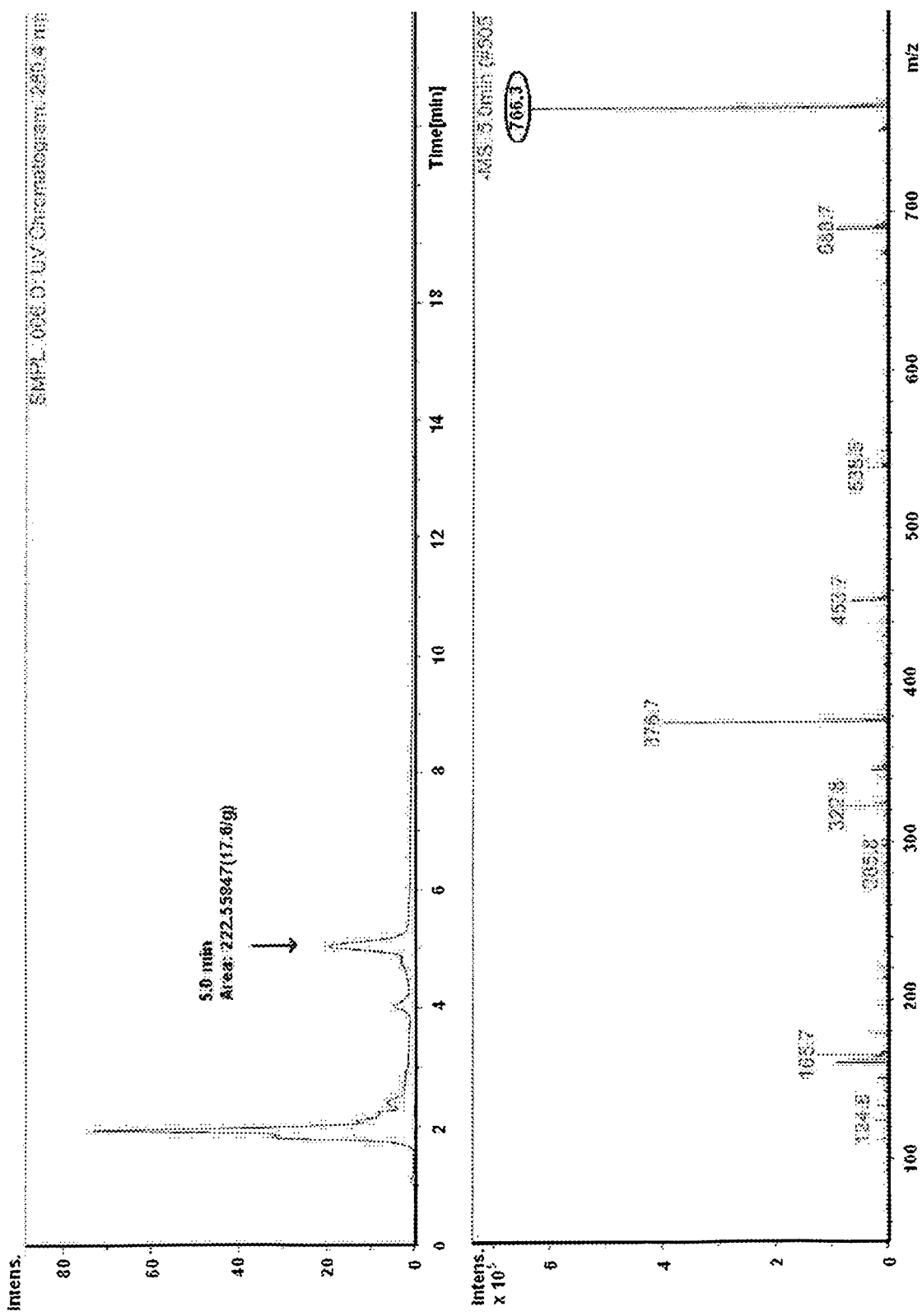
FIG. 6 shows the result of LC and Mass spectrum of ginseng extract (G6)
Figure 7:
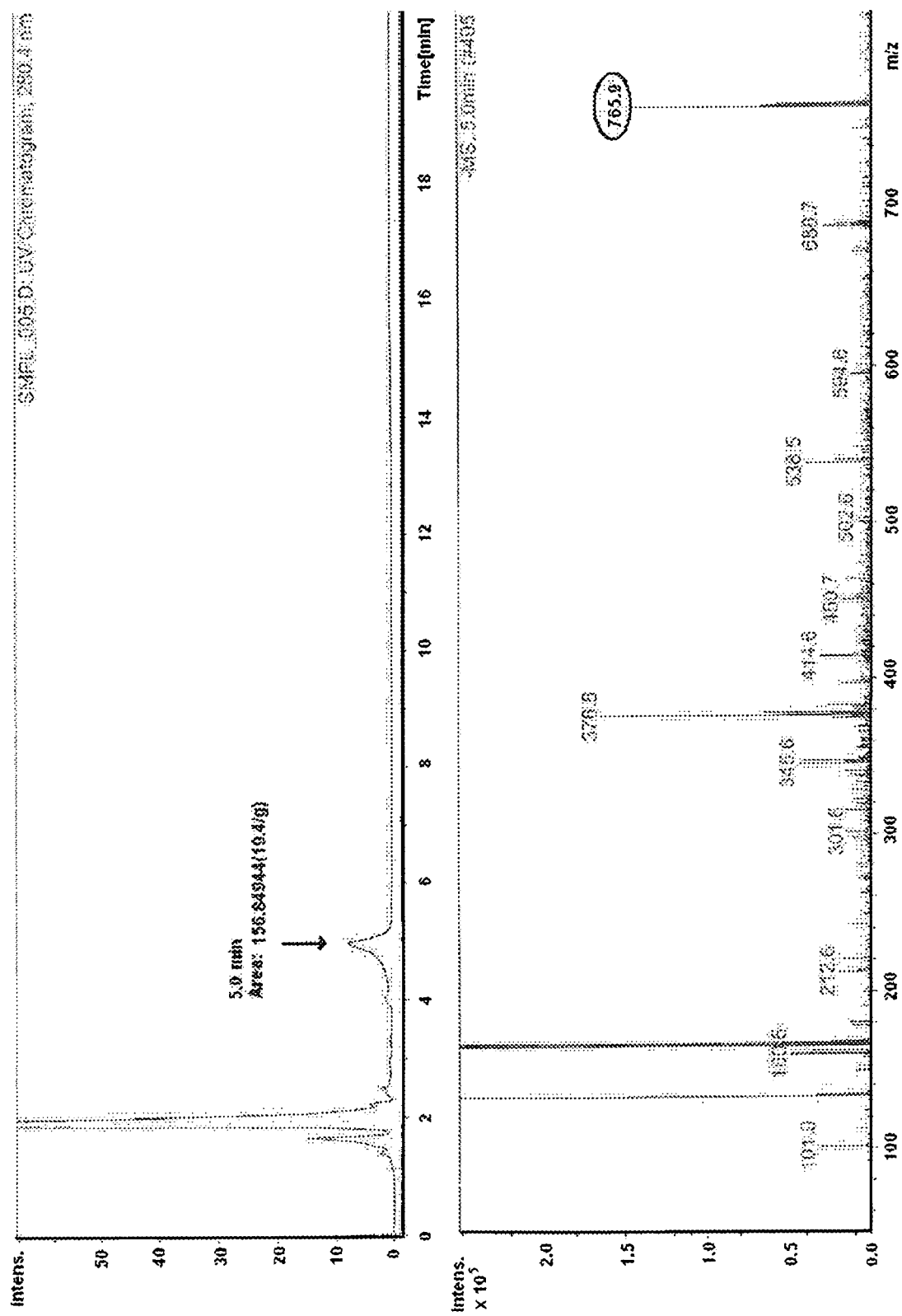
FIG. 7 shows the result of LC and Mass spectrum of ginseng extract (STD).

The present invention is more specifically explained by the following examples. However, it should be understood that the present invention is not limited to these examples in any manner.

COMPARATIVE EXAMPLE 1

Preparation of the Processed Ginseng According to the Procedure Disclosed in KR Patent Registration 10-0192678

Non-dried and sliced 1 kg of *Panax ginseng* root was placed into crude drug extraction apparatus (20 L/Kukjekigong, Korea) and then was heated by steaming at 130° C. for 2 hours. The steamed ginseng was dried at 50-60° C., and pulverized into fine powder with the powder size ranging from 50-200 micrometer to obtain 195 g of ginseng powder used as a comparative sample (designated as "STD" hereinafter).

EXAMPLE 1

Preparation of Inventive Ginseng (1)

Air-dried and sliced 300 g of six years old un-husked *Panax ginseng* root dipped into 600 ml of distilled water was placed into crude drug extraction apparatus (20 L/Kukjekigong, Korea) and then was heated maintaining the internal temperature ranging from 126° C. to 130° C. and internal pressure ranging from 1.4 to 1.5 kgf/cm$^2$ for 2 hours. The processed ginseng was isolated from the water and dried with at 60-70° C., and pulverized into fine powder with the powder size ranging from 50-200 micrometer to obtain 255 g of ginseng powder (yield: 85.0%) used as a sample (designated as "G1" hereinafter).

EXAMPLE 2

Preparation of Inventive Ginseng (2)

All the procedure excepting that the internal pressure was adjusted to 1.85 to 2.0 kgf/cm$^2$ was similar to those disclosed in Example 1 to obtain 245 g of ginseng powder (yield: 81.7%) used as a sample (designated as "G2" hereinafter).

EXAMPLE 3

Preparation of Inventive Ginseng (3)

All the procedure excepting that the internal pressure was adjusted to 2.30 to 2.50 kgf/cm$^2$ was similar to those disclosed in Example 1 to obtain 240 g of ginseng powder (yield: 80.0%) used as a sample (designated as "G3" hereinafter).

EXAMPLE 4

Preparation of Inventive Ginseng (4)

All the procedure excepting that the internal pressure was adjusted to 2.80 to 3.00 kgf/cm² was similar to those disclosed in Example 1 to obtain 235 g of ginseng powder (yield: 78.3%) used as a sample (designated as "G4" hereinafter).

EXAMPLE 5

Preparation of Inventive Ginseng (5)

All the procedure excepting that 300 g of six years old white ginseng was used and the internal pressure was adjusted to 2.80 to 3.00 kgf/cm² was similar to those disclosed in Example 1 to obtain 249 g of ginseng powder (yield: 83.0%) used as a sample (designated as "G5" hereinafter).

EXAMPLE 6

Preparation of Inventive Ginseng (6)

All the procedure excepting that 300 g of four years old un-husked ginseng was used was similar to those disclosed in Example 1 to obtain 236 g of ginseng powder (yield: 78.7%) used as a sample (designated as "G6" hereinafter).

Experimental Example 1

Analysis of Component and Content 1-1. Sample Preparation 20 ml of methanol and 20 ml of methylene chloride were added to each 2 g of the samples prepared from Comparative Example and Examples 1-6 and subjected to reflux extraction for 60 mins. The solution was cooled, filtrated to remove insoluble material and the supernatant was concentrated to obtain their residue. The weight of each final sample extract was 0.183 g (G1), 0.154 g (G2), 0.131 g (G3), 0.192 g (G4), 0.148 g (G5), 0.079 g (G6) and 0.124 g (STD) respectively.

1-2. LC Mass Analysis

The solvent mixture of methanol and methylene chloride (1:1) was added to test samples prepared in step 1-1 in an amount of 18.3 ml (G1), 15.4 ml (G2), 13.1 ml (G3), 19.2 ml (G4), 14.8 ml (G5), 7.9 ml (G6) and 12.4 ml (STD) respectively to the extent that the final sample concentration of each samples was adjusted to identical with each other. 3 ml of each sample was subjected to micro-centrifugation with a speed of 1300 rpm for 15 mins. 5 microliter of each supernatant was injected to LC Mass apparatus under the condition shown in Table 1 and the result was shown in FIGS. 1 to 7.

TABLE 1

| LC Mass Analysis | |
| --- | --- |
| Model | AGILENT: 1100 Series LC/MSD |
| Column | Microbonda Pak-NH₂; 3.0 × 390 mm (Waters) |
| Mobile Phase | $CH_3CN:H_2O:i-PrOH = 80:5:15$ |
| Flow Rate | 1.5 ml/min |
| Detection Wavelength | 280 nm |

The resulting comparison with each sample was shown in Table 2.

As can be seen in Table 1, it is confirmed that the amount of ginsenoside Rg5 prepared in Examples 1 and 5 are about 4.4 and 3.3 fold higher than that in Comparative Example.

Accordingly, it is confirmed that the preparation method of the present invention is superior to the method disclosed in the prior art.

TABLE 2

| Sample | Rg5 (peak area) | Residue weight (g) | Transformed Area/g | Rg5 (Area fold) |
| --- | --- | --- | --- | --- |
| G1 | 462.17697 | 0.183 | 84.6 | 4.4 |
| G2 | 265.28598 | 0.154 | 40.9 | 2.1 |
| G3 | 250.03737 | 0.131 | 32.8 | 1.7 |
| G4 | 280.65826 | 0.192 | 53.9 | 2.8 |
| G5 | 431.97482 | 0.148 | 63.9 | 3.3 |
| G6 | 222.55847 | 0.079 | 17.6 | 0.9 |
| STD | 156.84944 | 0.124 | 19.4 | 1.0 |

Additionally, the present inventors have been investigated to find optimum extraction condition, especially, the mixture ratio of extracting solvent system by varying the mixture volume ratio of methanol and methylene chloride within the range from 0.60:1.40 to 1.20:0.80 and finally found that most efficient extraction condition among them is the solvent mixture of methanol and methylene chloride (1:1) of which electric conductivity constant is 20.75.

Accordingly, we have confirmed that most efficient extraction solvent system to obtain abundant ginsesnoside Rg5 is the solvent mixture of methanol and methylene chloride (1:1) to obtain abundant ginsenoside Rg5.

EXPERIMENTAL EXAMPLE 2

Determination of Anticancer Activity

The anticancer activity of the ginseng extract containing abundant ginsenoside Rg5 prepared in Experimental Examples was determined by following experiments.

Sample Preparation

The inventive ginseng extract extracted with methanol and methylene chloride solvent mixture (1:1) prepared by the method according to the procedure disclosed in Example 5 was used as a test sample by dissolving in distilled water (5 mg/ml).

Test Animals

Four weeks-old C57BL/6 mice weighing 10-15 g bred under identical circumstance were classified into two groups, i.e., 80 mice as test groups and 20 mice as control group. Test groups were treated with B16 melanoma cell line to occur cancer and control groups were not treated. The test groups were further classified into two groups, i.e., test group (1) 40 mice treated with only distilled water and test group (2) 40 mice treated with equivalent amount of inventive extract at 5$^{th}$ week and the control groups were also classified into two groups, i.e., control group (1) 10 mice treated with only distilled water and control group (2) 10 mice treated with equivalent amount of inventive extract at 5$^{th}$ week.

Test Procedure

Four weeks-old C57BL/6 mice weighing 10-15 g bred under identical circumstance were freely accessible to drink the solution comprising inventive extract prepared by above step in control group (2) and test group (2) after the delactation of the mice (four weeks after the birth). B16 melanoma cell was injected into the back side of mice subcutaneously in cancer occurred groups on tenth week after the birth.

B16 melanoma cells were sub-cultured in $CO_2$ incubator for 1 week and the floated cells diluted RMPI 1640 medium comprising 10% fetal calf serum adjusted to $1\times10^6$ cells/ml were injected by 0.1 ml.

The cancer growth rate and survival period was determined by the size of cancer every five days after the injection and the survival period of each group. The cancer growth rate was compared with the weight of cancer and the result was calculated by the following empirical formula 1.

The weight of cancer (mg)=[the length of long length (mm)×the length of short length (mm)] ÷2    Empirical Formula 1

Test Result

Figure 8:
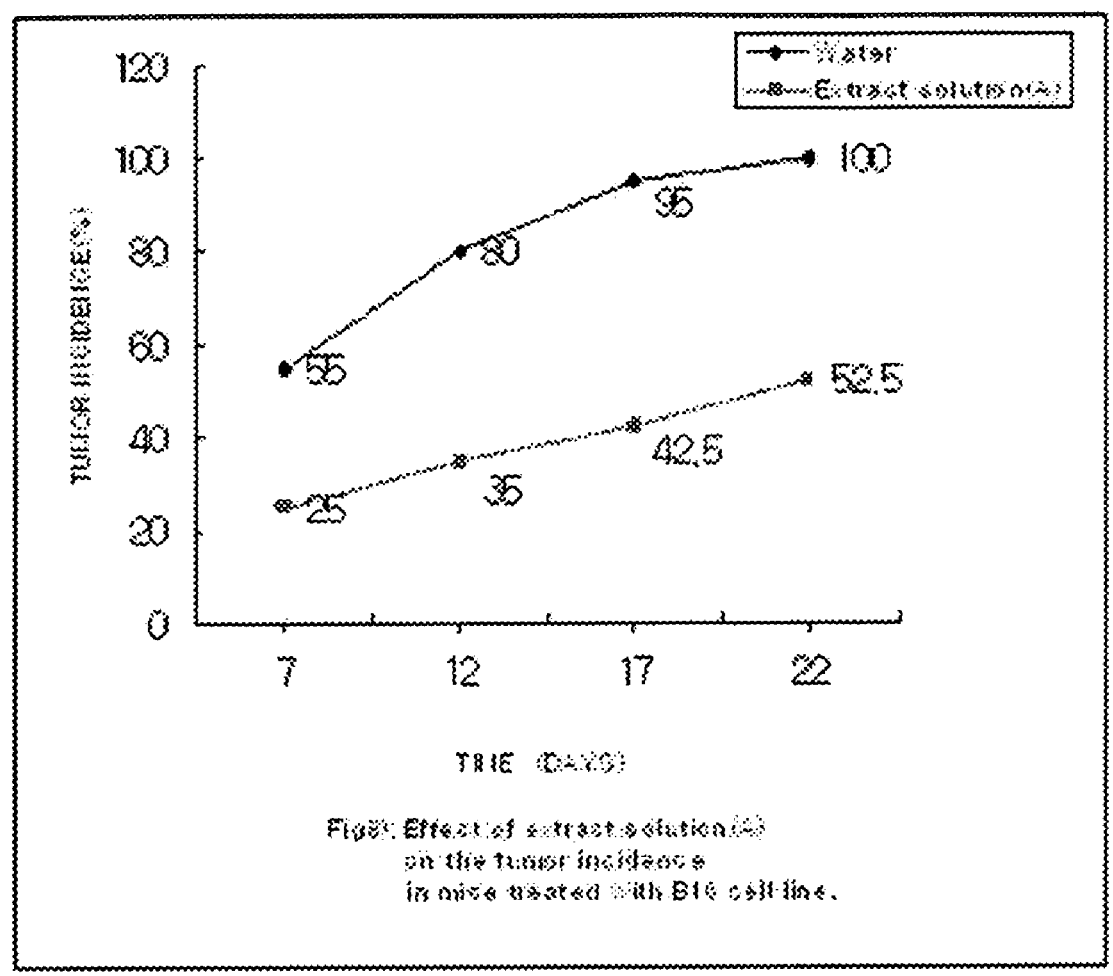
FIG. 8 represents the anticancer activity of the ginseng extract.

As can be seen in FIG. 8, 55% mice occurred cancer in test group (1) while 25% mice in test group (2) at 1 week. At the $12^{th}$ day and $17^{th}$ day, 80% and 95% mice occurred cancer in test group (1) respectively while 35% and 42.5% in test group (2) respectively. At the $22^{th}$ day, 100% mice occurred cancer in test group (1) while 52.5% in test group (2).

After B16 melanoma cells were injected in test group (1) and test group (2), the differentiation of cancer weight and survival ratio depends on days were as follows:

TABLE 3

| Group\Days\Item | Cancer Weight(g) | | | | | Survival Ratio(%) | | | |
|---|---|---|---|---|---|---|---|---|---|
| | 7 | 12 | 17 | 22 | 57 | 12 | 17 | 42 | 60 |
| Test Group(1) | 0.1 | 0.4 | 1.8 ± 0.3 | 5.1 ± 1.2 | 22.4 ± 5.3 | 100 | 97.5 | 50 | 0 |
| Test Group(2) | 0.1 | 0.3 | 1.5 ± 0.2 | 3.3 ± 1.0 | 9.8 ± 2.1 | 100 | 100 | 85 | 60 |

Accordingly, it is confirmed that the ginseng extract prepared by inventive method in the present invention showed potent anti-cancer activity since the method of the present invention could provide with abundant ginsenoside Rg5 which has potent anticancer activity.

Hereinafter, the formulating methods and kinds of excipients will be described, but the present invention is not limited to them. The representative preparation examples were described as follows.

| Preparation of powder | |
|---|---|
| Dried powder of Example 1 | 20 mg |
| Lactose | 100 mg |
| Talc | 10 mg |

Powder preparation was prepared by mixing above components and filling sealed package.

| Preparation of tablet | |
|---|---|
| Dried powder of Example 1 | 20 mg |
| Corn Starch | 100 mg |
| Lactose | 100 mg |
| Magnesium Stearate | 2 mg |

Tablet preparation was prepared by mixing above components and entabletting.

| Preparation of capsule | |
|---|---|
| Dried powder of Example 2 | 10 mg |
| Crystalline cellulose | 100 mg |
| Lactose | 100 mg |
| Magnesium Stearate | 2 mg |

Tablet preparation was prepared by mixing above components and filling gelatin capsule by conventional gelatin preparation method.

| Preparation of injection | |
|---|---|
| Extract of Example 5 | 10 mg |
| Distilled water for injection | optimum amount |
| PH controller | optimum amount |

Injection preparation was prepared by dissolving active component, controlling pH to about 7.5 and then filling all the components in 2 ml ample and sterilizing by conventional injection preparation method.

| Preparation of liquid | |
|---|---|
| Extract of Example 3 | 0.1~80 g |
| Sugar | 5~10 g |
| Citric acid | 0.05~0.3% |
| Caramel | 0.005~0.02% |
| Vitamin C | 0.1~1% |
| Distilled water | 79~94% |
| $CO_2$ gas | 0.5~0.82% |

Liquid preparation was prepared by dissolving active component, filling all the components and sterilizing by conventional liquid preparation method.

| Preparation of health care food | |
|---|---|
| Dried powder of Example 1 | 1000 mg |
| Vitamin mixture | optimum amount |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |

| Preparation of health care food | |
|---|---|
| Amide nicotinic acid | 1.7 mg |
| Folic acid | 50 μg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above mentioned vitamin and mineral mixture may be varied in many ways. Such variations are not to be regarded as a departure from the spirit and scope of the present invention.

| Preparation of health beverage | |
|---|---|
| Extract of Example 2 | 1000 mg |
| Citric acid | 1000 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

The method for preparing processed ginseng according to present invention could provide abundant amount ginsenoside Rg5 showing various pharmacological activities with applying selected specific pressure and temperature into the method and the composition comprising the processed ginseng and the extract thereof can be useful as a medicament or health care food in the prevention or treatment of various diseases, cancer, particularly.

The invention claimed is:

1. A method of preparing a processed ginseng extract comprising of the steps; adding about 1 to 5 times weight of water to five to seven years old ginseng material; and treating under an internal pressure ranging from 1.10 to 3.50 kgf/cm$^2$, at a temperature from about 100° C. to about 150° C., for 1 to 5 hours to obtain a processed ginseng; extracting the processed ginseng with a mixture of methanol and methylene chloride having a ratio from 0.60:1.40 to 1.20:0.80 with reflux extraction for a period from 1 hour to two days; filtering to obtain a filtrate; concentrating the filtrate to remove remaining solvent and drying to obtain said ginseng extract.

2. The method of claim 1, wherein said internal pressure ranges from 1.40 to 1.50 kgf/cm$^2$ in case of un-husked ginseng.

3. The method of claim 1, wherein said internal pressure ranges 2.80 to 3.00 kgf/cm$^2$ in case of husked ginseng.

4. The method of claim 1, wherein said temperature ranges from 126° C. to 130° C.

5. The method of claim 1, wherein said weight of water is an amount ranging 1 to 2 times weight of ginseng material.

6. The method of claim 1, wherein said period is about 2 hours.

7. The method of claim 1, said ginseng material is six years old un-husked ginseng or husked ginseng.

8. A pharmaceutical composition comprising a ginseng extract and a pharmaceutically acceptable carrier or adjuvants for the treatment of cancer disease, of which ginseng extract is prepared by a method comprising: adding about 1 to 5 times weight of water to five to seven years old ginseng material and treating under an internal pressure ranging from 1.10 to 3.50 kgf/cm$^2$, at a temperature ranging from about 100° to 150° C., for about 1 to 5 hours to obtain processed ginseng; extracting the processed ginseng with a mixture of methanol and methylene chloride having a ratio from 0.60:1.40 to 1.20:0.80 with reflux extraction for a period from 1 hour to two days; filtering to obtain filtrate, concentrating the filtrate to remove remaining solvent and drying to obtain said ginseng extract.

9. The pharmaceutical composition of claim 8, wherein said composition is provided as powder, granule, tablet, capsule, soft capsule, aqueous medicine, syrup, elixirs, pill, solution, powder, sachet, granule, cream, ointment, lotion, gel, balm, patch, paste, spray solution, aerosol or injection.

10. The pharmaceutical composition of claim 8, wherein the internal pressure is selected from the group consisting of 1.40 to 1.50 kgf/cm$^2$ for un-husked ginseng and 2.80 to 3.00 kgf/cm$^2$ for husked ginseng.

11. The pharmaceutical composition of claim 8, wherein the temperature ranges from 126° C. to 130° C.

12. The pharmaceutical composition of claim 8, wherein the weight of water is an amount ranging 1 to 2 times weight of ginseng material.

13. A health care food comprising a ginseng extract and a sitologically acceptable food additive, of which ginseng extract is prepared by a method comprising; adding about 1 to 5 times weight of water to five to seven years old ginseng material; and treating under an internal pressure ranging from 1.10 to 3.50 kgf/cm$^2$, at a temperature ranging from about 100° to 150° C., for 1 to 5 hours to obtain processed ginseng; extracting the processed ginseng with a mixture of methanol and methylene chloride having a ratio from 0.60:1.40 to 1.20:0.80 with reflux extraction for a period from 1 hour to two days; filtering to obtain filtrate, concentrating the filtrate to remove remaining solvent and drying to obtain said ginseng extract.

14. The health care food of claim 13, wherein said health care food is provided as a tablet, capsule, powder, or granule.

15. The health care food of claim 13, wherein the internal pressure is selected from the group consisting of 1.40 to 1.50 kgf/cm$^2$ for un-husked ginseng and 2.80 to 3.00 kgf/cm$^2$ for husked ginseng.

16. The health care food of claim 13, wherein the temperature ranges from 126° C. to 130° C.

17. The health care food of claim 13, wherein the weight of water is an amount ranging 1 to 2 times weight of ginseng material.

* * * * *